United States Patent
Stier et al.

(10) Patent No.: US 10,426,650 B2
(45) Date of Patent: Oct. 1, 2019

(54) RECLINER-TYPE ORTHOSIS COMPRISING TIGHTENING STRAPS

(71) Applicant: Bauerfeind AG, Zeulenroda-Triebes (DE)

(72) Inventors: Gerald Stier, Langenwetzendorf (DE); Jürgen Harms, Karlsruhe (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 0 days.

(21) Appl. No.: 16/072,740

(22) PCT Filed: Jan. 27, 2017

(86) PCT No.: PCT/EP2017/051803
§ 371 (c)(1),
(2) Date: Jul. 25, 2018

(87) PCT Pub. No.: WO2017/129762
PCT Pub. Date: Aug. 3, 2017

(65) Prior Publication Data
US 2019/0029866 A1  Jan. 31, 2019

(30) Foreign Application Priority Data
Jan. 28, 2016  (DE) .................. 10 2016 201 270

(51) Int. Cl.
*A61F 5/02* (2006.01)
(52) U.S. Cl.
CPC .............. *A61F 5/026* (2013.01); *A61F 5/028* (2013.01)

(58) Field of Classification Search
CPC .. A61F 5/02; A61F 5/022; A61F 5/024; A61F 5/026; A61F 5/028; A41C 1/00;
(Continued)

(56) References Cited

U.S. PATENT DOCUMENTS 690,096 A * 12/1901 Bower
940,775 A * 11/1909 Adams
(Continued)

FOREIGN PATENT DOCUMENTS

DE  10329454 A1  1/2005
EP  2070495 A1  6/2009
(Continued)

OTHER PUBLICATIONS

PCT International Search Report and Written Opinion dated May 9, 2017 for PCT/EP2017/051803 (12 pages).

*Primary Examiner* — Kari K Rodriquez
(74) *Attorney, Agent, or Firm* — Carter, DeLuca & Farrell LLP; George Likourezos (57) ABSTRACT

The invention relates to a recliner-type orthosis comprising a lap belt or pelvic strap (30), a rigid recliner rail (10) over the spinal column, and two individually tightenable shoulder straps (23, 24), each of which extends from a lower portion (12) of then recliner rail (10), forms a shoulder strap, and is guided backwards via guides (18, 19) on a top portion (14) of the recliner rail (10), where the two shoulder straps (23, 24) intersect in a central point of intersection (29) and then run contralaterally towards the front, intersect in lateral points of intersection (27, 28) and can finally be tightly attached to the lap belt (30).

20 Claims, 7 Drawing Sheets

(58) Field of Classification Search
CPC ........ A41C 1/02; A41C 1/08; A41D 13/0512; A41D 13/0525; A41D 13/053
See application file for complete search history.

(56) References Cited

U.S. PATENT DOCUMENTS

| | | | |
|---|---|---|---|
| 945,359 A | | 1/1910 | Adams |
| 996,343 A | * | 6/1911 | Johnson |
| 1,100,499 A | * | 6/1914 | Small ................ A61F 5/026 2/310 |
| 1,386,067 A | * | 8/1921 | Mason ............... A61F 5/026 2/45 |
| 1,532,304 A | * | 4/1925 | Cunning ............ A61F 5/026 2/45 |
| 3,282,264 A | * | 11/1966 | Connelly ........... A61F 5/026 450/96 |
| 7,833,182 B2 | | 11/2010 | Hughes |
| 2008/0228121 A1 | | 9/2008 | Hughes |
| 2010/0318010 A1 | | 12/2010 | Sandifer et al. |
| 2011/0105971 A1 | * | 5/2011 | Ingimundarson ....... A61F 5/024 602/19 |
| 2012/0245501 A1 | | 9/2012 | Rossi et al. |
| 2014/0018715 A1 | * | 1/2014 | Ingimundarson ....... A61F 5/026 602/19 |
| 2014/0221893 A1 | * | 8/2014 | Modglin ................ A61F 5/028 602/19 |
| 2015/0133843 A1 | * | 5/2015 | Turrini .................. A61F 5/026 602/19 |
| 2016/0038331 A1 | * | 2/2016 | Petterson ............. A61B 5/1116 602/19 |

FOREIGN PATENT DOCUMENTS

| | | |
|---|---|---|
| GB | 2159058 A | 11/1985 |
| WO | 2007043079 A1 | 4/2007 |
| WO | 2009052031 A1 | 4/2009 |

* cited by examiner

RECLINER-TYPE ORTHOSIS COMPRISING TIGHTENING STRAPS

FIELD OF THE INVENTION

The invention relates to a back brace to extend a curved spine or to treat and correct posture errors particularly in the upper back area by repositioning the shoulders. A novel reclination orthosis having a special strap run is provided, whose function is most effective, and can be easily applied and adjusted.

BACKGROUND

Reclination orthoses, also called vertebrate extension orthoses, essentially consist of a rigid splint element, which runs along the spine ("reclinator"), which is pressed to the spine via straps and bandages, which embrace the patient's body while being under tension to provide a supporting effect at that location. Known reclination orthoses encompass the shoulder areas by means of two shoulder straps, and pull the shoulders backwards when worn. Through the interaction of the shoulder straps, the reclinator, and body-embracing bandage the patient's spine is mechanically stabilized, and the shoulder area and upper thoracic spine area is straightened up in particular. The tighter the shoulder straps are tensed, the more the shoulders are pulled backwards, which straightens out the upper body. The key support aspect of known reclination orthoses is effected in the area of the upper vertebrae of the chest up to the vertebrae of the neck. However, in the case of degenerative disorders of the spine, particularly in case of osteoporosis, i.e. a weakening of all bodies of the vertebra, it becomes necessary to mechanically support the spine in the area of the lower vertebrae of the chest, the vertebrae of the loin and/or of the sacral bone, and to straighten it out, if necessary. Known reclination orthoses are yet unable to realize this in an adequate manner.

In addition, a complex structure, and a rigid elaboration of the bandages and tension straps, which are merely designed to provide a specific supporting effect but which do not adequately allow a custom adjustment to a specific indication position, to therapeutic requirements, and/or to any given anatomic conditions are disadvantageous in known reclination orthoses. In particular, the supporting effect fails to materialize depending on the movement phase when patients move, because known reclination orthoses are unable to adequately follow the movements. Moreover, patients have difficulties in applying known reclination orthoses, because they are unable to excert the mechanical force, particularly the traction or tension, required to attain the straightening and supporting effect. This constitutes a particular handicap for older patients.

SUMMARY

The present invention is based on the technical problem to provide an improved reclination orthosis, which would be able to provide a supporting effect along the entire length of the spine up to the pelvis, which can be adjusted specifically to the patient, and which he can apply easily for an effect that would produce results. The technical problem is fully solved by a reclination orthosis in accordance with the claims, thus particularly a reclination orthosis having a rigid reclinator splint, which, when applied runs along the entire spine, a pelvic strap, which is mounted on the iliac crest and pelvis in particular and which can encompass the pelvis, as well as two solitary, particularly free-range, tensible shoulder straps. The reclination orthosis in accordance with the invention preferably consists exclusively of these supporting, force-introducing elements without any additional bandages and strap elements, apart from dependent passive auxiliary applications such as padding, pelottes, strap guides, and interlocking systems.

The straps of the reclination orthosis in accordance with the invention provide a unique and novel strap route around the patient's body, including a minimum of three actual strap crossings. According to the invention, both straps start from a caudal and particularly low placed section of the reclinator splint. They proceed from there towards cranial, i.e. the top, along the ipsilateral body flank on the patient's chest, that is, under the patient's armpit, over the respective ipsilateral front shoulder, respectively, where they form shoulder strap sections, respectively, then back towards dorsal while passing a cranial section of the reclinator splint, where they are guided freely in guides towards caudal, i.e. downwards. The straps cross at a central, dorsal, cranial cross point, and then caudally to contralaterally, respectively, that is, at the contralateral body flank at the patient's chest, that is, along under the arm pit while pulling ventrally. The contralaterally running strap is at a lateral thoracic cross point, which is preferably located between the arm pit and iliac crest, and crosses with the respective ispsilaterally rising strap partner. Finally, the contralaterally running straps run towards the lateral thoracic crossing ventrally ending in strap ends, respectively, which can be directly affixed while under tension at the pelvic strap's ventral section of the orthosis.

Thus, the reclination orthosis according to the invention will be initially applied using two solitary shoulder straps in the manner of a backpack, and tightened to the body at the pelvis by means of a pelvic strap, which is firmly connected to the reclinator splint. The loose strap ends of the individual straps that are affixed at the caudal section of the reclinator splint can be pulled and tensed individually, whereby the pulling force can distribute itself automatically by means of the particularly free running straps onto important pressure introduction points of the orthosis, namely: front shoulder/collar bone—cranial section of the reclinator splint—caudal section of the reclinator splint—pelvic strap, thus creating a traction cycle that is closed in on itself, respectively. The straps form each shoulder strap sections, in the shoulder area, where from the introduction of the main force to the body takes place. Thus, the shoulder can be pulled backwards as required for treatment, and the reclinator splint is pulled concurrently to the spine so that the upper thoracic and cervical spine can be straightened.

The supporting effect of the reclinators also extends to the lower thoracic spine, the lumbar part of the spine, and the sacral bone by means of the pelvic strap, which always runs here particularly in accordance with the invention below the patient's belly and particularly at the level of the ileosacral joint, and which is firmly connected to the cranial section of the reclinator splint at least at that point. An unprecedented freedom of movement for the patient is advantageously made possible due to the particularly free strap guide of both body-revolving shoulder straps, which are respectively fixed or fixable only at the caudal section of the reclinator splint on the one side, and at the ventral section of the pelvic strap on the other side. The orthosis is concurrently positioned in a stable manner at the body, and continually adjusts itself to the movement phases by means of the closed traction cycle in a dynamic manner.

Particularly, a dynamic force distribution that depend on the patient's movement and posture, is advantageously implemented at the pressure introduction points which secures the supporting effect and reclination in each movement phase and increases the patient's wear comfort at the same time. This dynamic distribution of force allows the patient to actively adopt an upright posture while moving, and supports consciously or partially reflexively the reclination orthosis' supporting effect by means of an active muscle activity. In particular, the novel strap route forms additional particularly solitary pressure introduction points in the pelvis frame area, in the front iliac crest area, and particularly at both thoracic lateral strap crossings at the chest sides as well, which can also contribute to a reflex activation of the muscular support system. The feared disadvantage of known static support orthoses, namely a weakening of the support muscles will not only be avoided when using the reclination orthosis in accordance with the invention having a dynamic force distribution and pressure introduction, but rather, a training effect will be achieved for the muscular support system. This is of great benefit particularly for rehabilitation efforts after accidents for instance, or spine injuries of a different type, for instance after surgery. At the same time, the reclination orthosis according to the invention achieves these benefits by means of a simple mechanical build and a low number of specific components.

In a preferred embodiment, the fixation points of both shoulder straps at the reclinator splint, in the area of the reclinator splint's caudal sections can be freely selected. In particular, several fixation points are provided at that point, where anchor grommets through which the straps are guided and fastened on them, respectively, can be fixed in a position of choice.

Although a characteristic of the invention provides for a deep leverage point of both body encompassing shoulder straps, preferably in the area of the ileosacral-joint, at the dorsal pelvis section of the patient, whereby the straps at the positionable caudal section of the reclinator splint or the pelvic strap have been fixed there or are fixable there, the height of this caudal strap edge along the reclinator splint can be changed. This specifically serves to adapt the reclination orthosis' treatment effect on the one hand, alternatively or additionally to an adaptation to the body height and to the anatomic conditions, particularly the torso's length, pelvic size, and on the other hand, it for instance serves patients having significantly shortened vertebral bodies due to degenerative diseases. Thus, an orthopedic technician can revise these patient parameters when adjusting the orthosis and then select the respective favorable starting point of both straps in the reclinator splint's caudal section, which allows an appropriate pressure introduction and force distribution for each respective treatment. The free strap ends guided through the anchor grommets are preferably variable, can be attached to themselves, for instance by means of a hook and loop fastener or by buttoning, hooking. Thus the straps' entire length can be easily adapted. In a specific embodiment, the anchor grommets are formed as gripping double eyelets, which allows for a continuously variable adjustment of the strap's length having an automatic deadlock at the anchor grommets.

In a preferred embodiment, guide grommets, i.e. guide elements for the straps, are particularly provided at the top, i.e. the reclinator splint's cranial section, through which the straps can slide particularly freely. In a preferred variant, these guides or guide grommets can be attached at the cranial section of the reclinator splint whereby their position can be varied. In a preferred variant, several recesses that are spaced to each other are provided at or in the reclinator splint through which the straps may slide. In an alternative variant, separate guide grommets are provided there, which can be fixed on the reclinator splint in variable positions, particularly by means of a hook and loop fastener, buttoning or screwing. In accordance with the invention, these guide elements serve as guides and concurrently as turn-around points on the straps at the reclinator splint's cranial section. The guides are used to introduce force at that place into the reclinator splint after the straps had been tightened. By varying the guide element's position at the reclinator splint, the introduction of force may be adapted to the treatment's objective and/or to the patient's proportions. In a preferred version, the guide elements can be completely removed from the reclinator splint. Thus, the entire orthosis construction is easily dismountable, and the reclinator splint can be removed more particularly without the shoulder straps needing to be completely removed from the splint. Applying the orthosis can also be facilitated in this manner.

A particular characteristic of the reclination orthosis in accordance with the invention is the specific strap route of both solitary, particularly free-running straps, which each run from a caudal section of the reclinator splint, and which each laterally cross, under each of the patient's armpits across the chest in two lateral thoracic cross points, laterally on the patient's body at chest level under the armpits, with their contralateral strap partner essentially at a 90° angle. Ideally, the straps cross around the center of an assumed line between the arm pit and iliac crest, respectively, and especially preferably even below the center of this line in the direction of the iliac crest. In a preferred variant thereof, the straps are guided on these lateral cross points in special cross guides, whereby a crossing angle of about 90° has been specifically preset. These cross guides are specifically formed in a preferred embodiment of the reclination orthosis in accordance with the invention, to allow at least one of the straps, preferably both straps, to freely slide in guide grommets or appropriate recess, which are formed thereon, so that the crossing of both straps at the cross point "finds" itself after applying the reclination orthosis and after tensing both straps. This "self-finding" lateral crossing of the straps in the area between arm pit and iliac crest, which is preferred in accordance with the invention, allows and/or supports the dynamic pressure distribution at the reclination orthosis, which can be achieved in accordance with the invention. This mechanic cross guide also facilitates applying and tensing the reclination orthosis on the patient and above all by the patient by means of both loose and fixable strap ends of these shoulder straps, which encompass the patient's body and which are crossing in accordance with the invention.

In addition, these cross guides can be provided on the body side with padding and specifically with an additional pressure-introducing pelotte. This pelotte preferably supports the dynamic pressure distribution on the applied reclination orthosis for purposes of an active improvement of the posture.

In an alternative variant, these cross guides are specifically formed to fix at least one of both, particularly preferably, both guided straps in place. Appropriate strap clips or notches may be formed there. Thus, depending on the therapeutic approach and/or anatomic conditions, the dynamic "self-finding" of the cross points of both straps can be influenced or suppressed or fixated. When determining the cross guide on at least one of the two crossing straps, the cross guide itself can absorb shearing and tangential forces, and can have a local body-supporting effect, especially in connection with a pelotte. Alternatively or additionally, excessive shift of the patient's lateral cross point through the cross guide, which is to be fixed on at least one of the straps, depending on his movement condition can be avoided, for instance, a shift of the cross point too far towards the top in the directions of the armpits. In a particular embodiment of the cross guides, they are formed in such manner that the straps can be recurrently alternated between freely passing through the straps and being locally fixated. An orthopedic technician can thus, for instance, select the appropriate function when adjusting the reclination orthosis on the patient. In particular, it has been provided, however, that the straps in the cross guides run freely initially, while the reclination orthosis is applied on the patient, that the shoulder straps be subsequently tensed, and that—after the lateral cross points "found" each other during the application—the straps can now be attached at the cross guides in the functional condition in order to prevent a shifting of the found cross points, for instance during excessive movements when performing athletic activities, or physiotherapeutic exercises.

The pelvic strap, with which the reclinator splint is preferably firmly attached, is indeed preferably formed in a known fashion per se: two wide bandage straps stretch, respectively, to both sides of the reclinator splint, and can be guided around the torso and locked. But this pelvic strap is specifically formed, so that it can be guided around the iliac crest and/or the pelvis and, while procuring tension, it can be closed across the lower abdomen/pubic bone while tensed. Overlapping bandage ends are preferred in this case, which can be attached to each other by means of a hook and loop fastener guaranteeing tensile strength. Using hooks and buttons to connect both bandage ends would be an alternative. In accordance with the invention, the orthosis' pelvic strap is also positioned very deep down on the torso; indeed, it is positioned at the iliac crest and below. This low application significantly supports the orthosis' reclination effect. It allows for a low application of both straps at the reclinator splint in the area of the ileosacral joint.

In a preferred embodiment, both bandage ends of the pelvic strap in the ventral section are additionally provided with means, which allow both tensed shoulder straps being fixed under tension at that location. Hook-and-loop-fastening elements are preferred; for instance, hook elements on the strap ends' body side, and fleece elements on the opposite surface. Thus, the bandage ends and both strap ends of the shoulder straps can simply be placed on top of each other and thus connected with each other in a manner that guarantees tensile strength. By means of an appropriately large hook and loop-fleece surface in the area of the ventral sections of the pelvic strap, a variable fixation of both strap ends, and thus a tensile stress variation, and thus an introduction of the force into the reclination orthosis will be facilitated. Thus, the patient can easily adjust the desired supporting effect of his reclination orthosis by himself depending on the treatment's objective and/or course on his movements. Alternative means to determine the strap ends in the ventral area of the pelvic strap would be buttoning and hooking.

In a preferred version, the strap ends of both shoulder straps are additionally provided with intervention possibilities in form of pockets or handles, which allow the patient to easily grab and tense the strap ends. This is of great advantage particularly for older patients whose manual mobility is limited.

In the embodiments of the reclination orthosis in accordance with the invention described here primarily, both shoulder straps/tension straps in accordance with the invention are formed in form of flat, flexible and essentially non-elastic strap bands. The bands' width is appropriately about 1 cm to about 10 cm, and preferably 2 cm to 6 cm. In the pressure introduction's main points' area, and particularly in the area of the front shoulder sections, in the area of the collar bone, the straps are preferably provided with padding elements or pelottes known per se to ensure a targeted introduction of pressure. They are preferably movable at the strap, and can thus be prepositioned on the body when applying the orthosis, whereby this padding will not move any more on the body during the subsequent tensioning of the straps, but rather, the straps can freely slide in the padding.

In particular versions thereof, the padding is attached to straps, respectively, and sowed on especially, in order to facilitate the reclination orthosis' application, particularly for patients whose movements are limited. Such strap padding is located at least in the area of the front shoulders of the collar bones. Additionally, padding in the area of the iliac crest is preferably provided at the place where the straps run ventrally towards the strap ends after passing the lateral thoracic crossings. Through the lateral crossing and fixation of the strap ends in the ventral section of the pelvic strap, an additional pressure introduction point is created preferably between the lateral cross point and the place of the ventral fixation of the strap ends.

In the reclination orthosis in accordance with the invention, this pressure introduction point is located in the area of the iliac crest; it supports the supporting function of the reclination orthosis in accordance with the invention particularly in the area the lower vertebra of the chest, the vertebrae of the loin, and the sacral vertebra. Without wanting to be bound to the theory, the additional pressure introduction point supports a force-fit connection of the reclinator splint with the pelvis and the caudal section of the spine, and particularly the ileosacral-joint in the ventral area of the iliac crest. Because of this pelvis-side force introduction, the reclination in the area of the upper vertebra of the chest and vertebra of the neck along with a concurrent dynamic pressure distribution will be improved retroactively as well due to the force fit via the running shoulder straps.

In an alternative embodiment, the shoulder straps according to the invention are formed additionally or exclusively as pull wires or pull cords, which are provided with padding and/or pelottes at the appropriate pressure introduction points. For instance, these pull cords can run being covered in textile channels that themselves can serve as padding. The arrangement of the straps as pull cords, which specifically run in textile channels, allows for an easy and particularly airy or breathable construction. Furthermore, the reclination orthosis can be folded into something smaller, and stored and presented for sale in smaller sales packages.

In a preferred embodiment, the reclinator splint consists of a rigid reclinator core, which is incorporated in a reclinator bag, preferably a textile bag, where it is kept in place. The bag is preferably sewn or welded to the pelvic strap. The bag serves to pad the rigid reclinator core and is additionally preferred to fixate additional specifically positionable padding and/or pelottes along the reclinator splint for a targeted therapeutically appropriate pressure introduction at the spine. The reclinator splint is preferably loosely inserted into this bag and can also be removed from it to be adapted immediately by an orthopedic technician to the treatment objective and/or to the patient's anatomic conditions without the orthosis needing to be completely dismantled or stripped down. Aluminum or a thermo-moldable plastic, particularly a rigid thermoplastic, which is particularly reinforced mechanically with carbon fiber, is the preferred material for the reclinator splint. Appropriate material is known from orthopedic technology and prosthetics for hot forming. Additionally, mechanically differing rigid arrangements of the reclinator core are provided that can be optionally placed into the bag depending on the treatment's objective.

DETAILED DESCRIPTION

Figure 1:
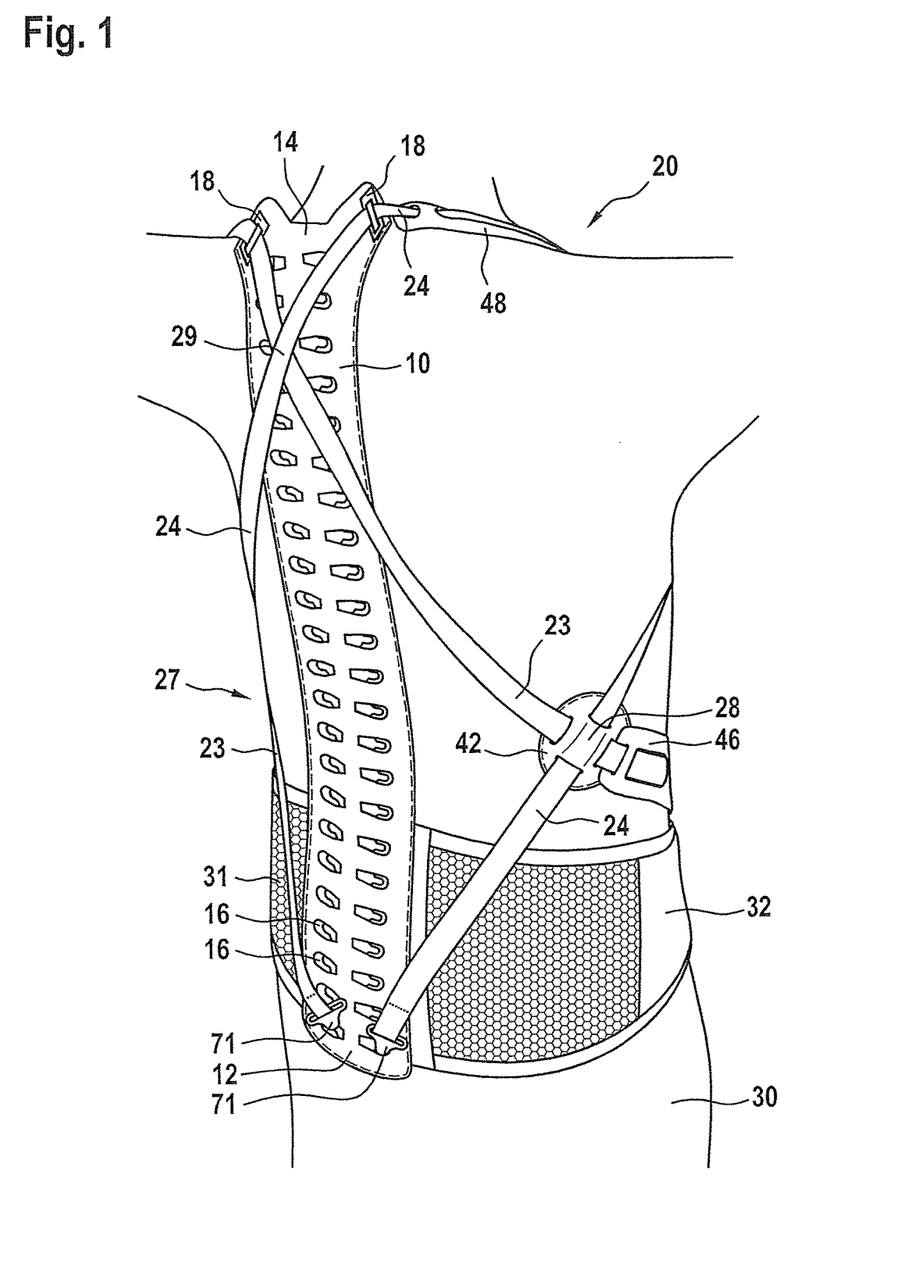
Figure 2:
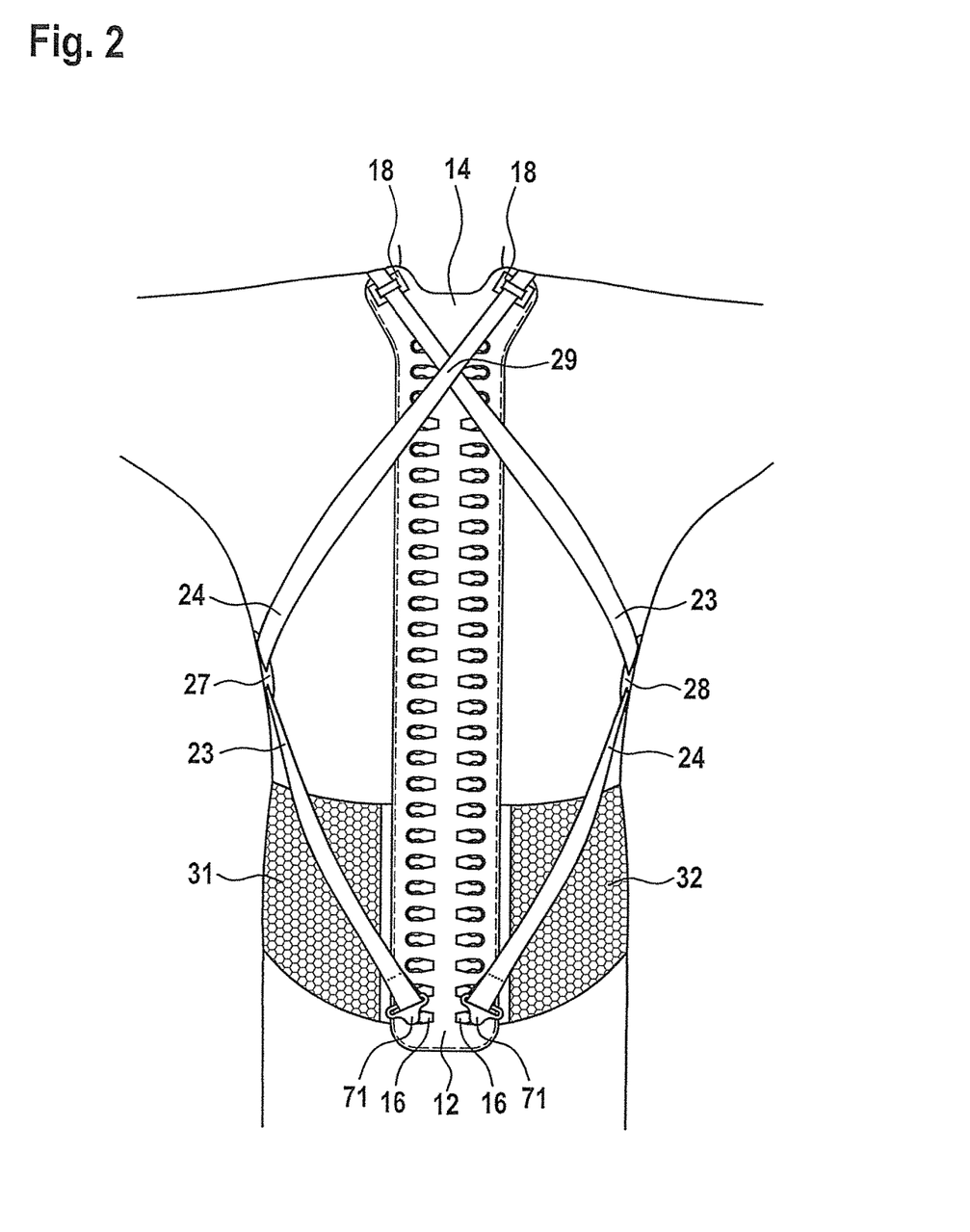

The invention will now be described in further detail using the embodiment examples without interpreting them as being specifically limiting. Any individual characteristics of the invention shown in the figures may be part of an embodiment of the invention by themselves and without any optional characteristics that were also depicted. FIG. 1 shows an oblique rear view of a reclination orthosis in accordance with the invention that has been applied to a patient. At pelvic strap or lap belt 30, both bandage ends 31, 32 are lockable around the pelvis in a manner guaranteeing tensile strength, and strap belt 30 is firmly connected with reclinator splint 10. Reclinator splint 10 consists of a reclinator core within a bag with windows. In caudal section 12 of the reclinator splint anchor points 16, anchor grommets 71 of straps 23, 24 are suspended. Straps 23, 24 run from these anchoring points 16 in caudal section 12 across the iliac crest at the patient's flank towards the front where they form shoulder strap section 20, respectively, and where they run across the front shoulder section back to dorsal via guides 18 at cranial section 14 of reclinator splint 10, and cross at dorsal central cross point 29 roughly in the middle and in the area of the upper vertebra of the patient's chest. Straps 23, 24 then run to the opposite side of the body and then cross at lateral thoracic cross points 27, 28 and end in ventral cranial strap ends 25, 26 (not depicted in FIG. 1), which can be attached at a ventral section of pelvic strap 30 while being tensed. At lateral thoracic cross points 27, 28 straps 23, 24 crossing there are guided in cross guides 42, which are provided with padding body-side. In addition, straps 23, 24 at the main points of the force introduction/ pressure introduction preferably wear different padding and/ or pelottes: padding 48 in the shoulder area, padding 46 in the iliac crest area. FIG. 2 depicts a frontal rear view of the situation according to FIG. 1.

Figure 3:
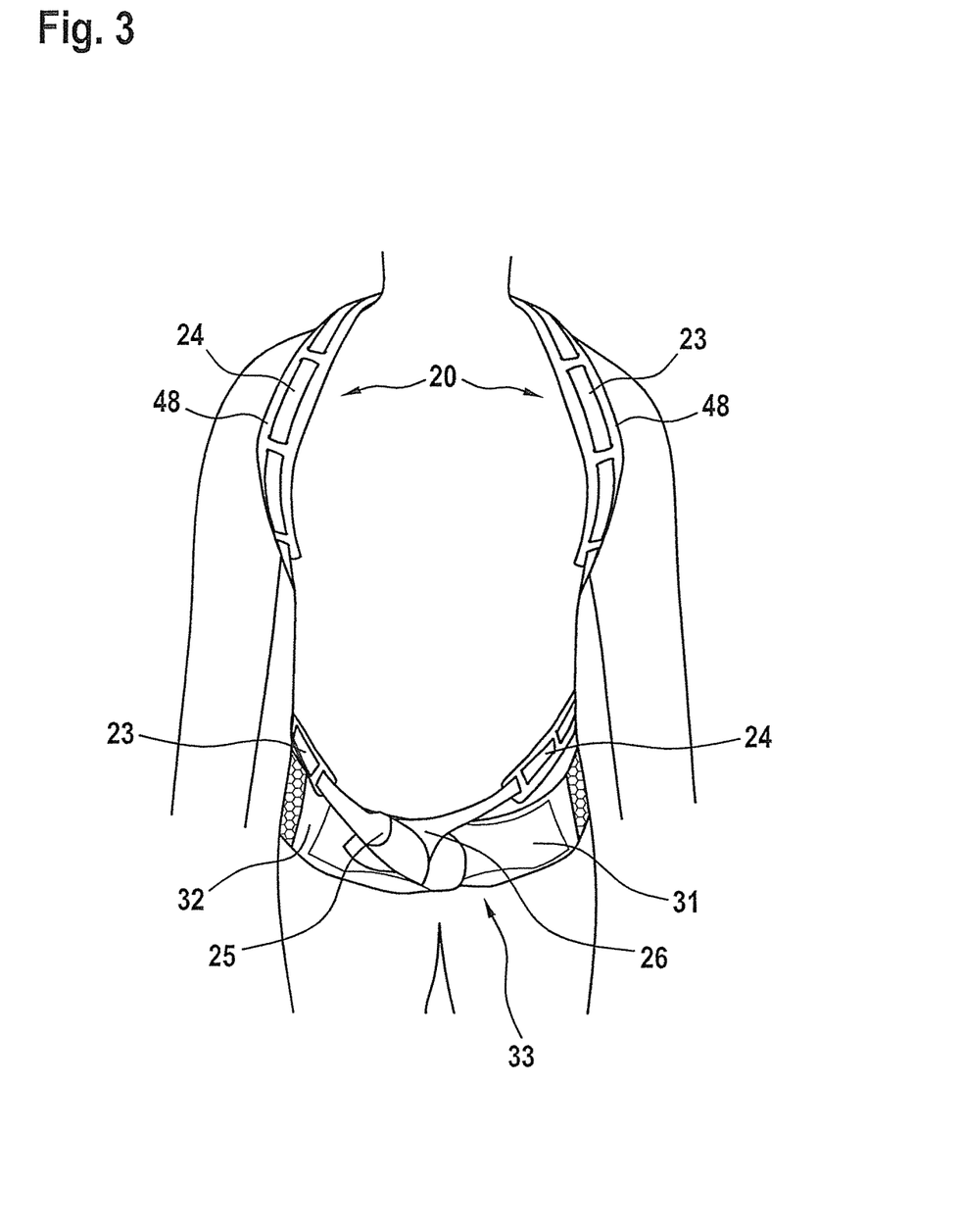

FIG. 3 shows the frontal view of the condition according to FIGS. 1 and 2. Both bandage ends 31, 32 of pelvic strap 30 are connected with each other by placing tensed hook and loop fastener elements on top of each other. The straps form shoulder strap sections in shoulder area 20, on which the principal introduction of the straps' force to the body is realized. In this depicted embodiment both strap ends 24, 25 of straps 23, 24 will be attached respectively there at the ventral section of pelvic strap 33, particularly on one of the two bandage ends 31, 32 also preferably by means of a hook and loop fastener. Pelvic strap 30 is placed distinctly below the belly button on the patient's iliac crest and pelvis. Bandage ends 31, 32 of the pelvic strap are locked in the area of the patient's lower abdomen or pubic bone.

Figure 4:
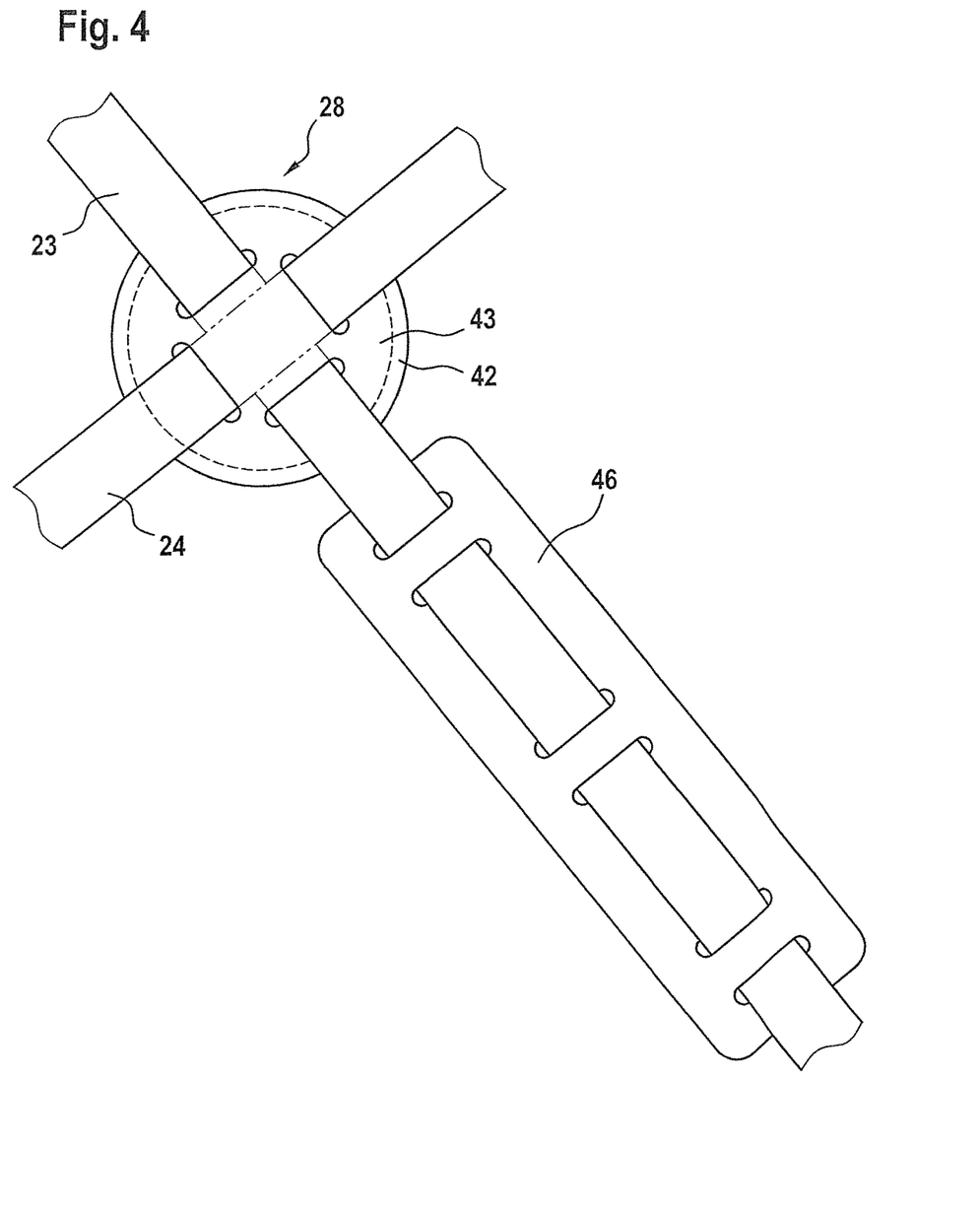

FIG. 4 shows a detailed view of the optional cross guides 42 including padding 43 below it at lateral thoracic cross point 28 of straps 23, 24. Additionally, padding element 46 at strap 23 exists, which can be positioned in the area of the front iliac crest thus creating an additional pressure introduction point there.

Figure 5A:
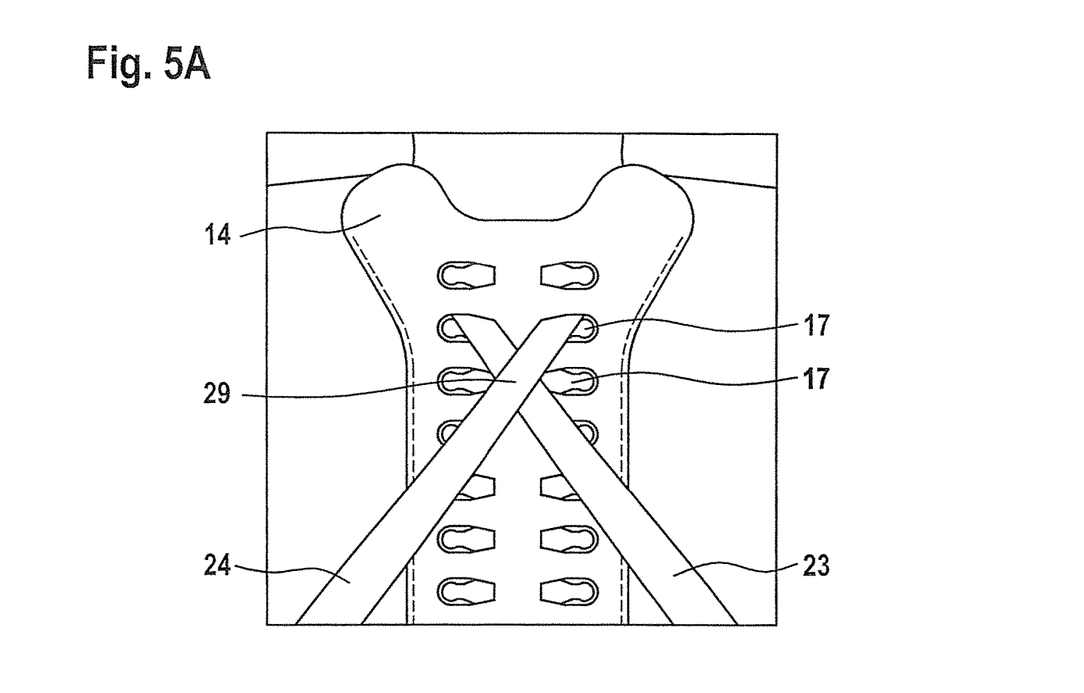
Figure 5B:
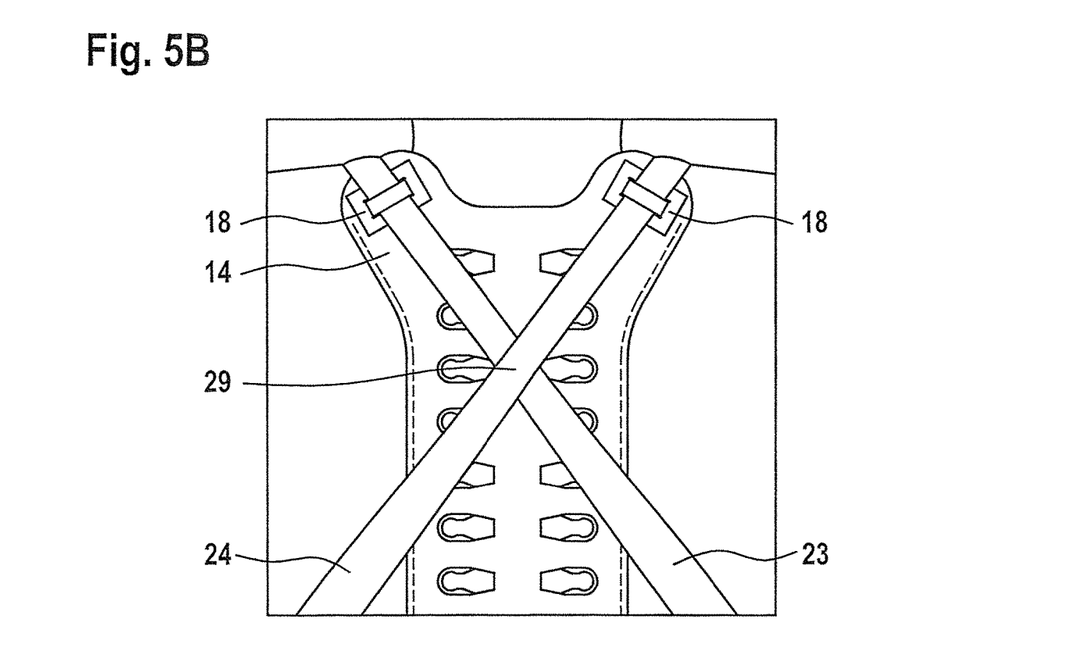

FIGS. 5A and 5B show various embodiments of the strap routes of shoulder straps 23, 24 in the area of cranial section 14 of the reclinator splint. FIG. 5A shows a version, where the straps are led through recesses in the reclinator splint where they preferably run freely. Several guides 17 which are spaced from each other can be provided at the reclinator splint to adapt the position of the strap route. An alternative and preferred embodiment is depicted in FIG. 5B, where separate guide grommets 18 guide the straps. The guide grommets' position may be arranged at the reclinator splint 10 such that it can be variable.

Figure 6:
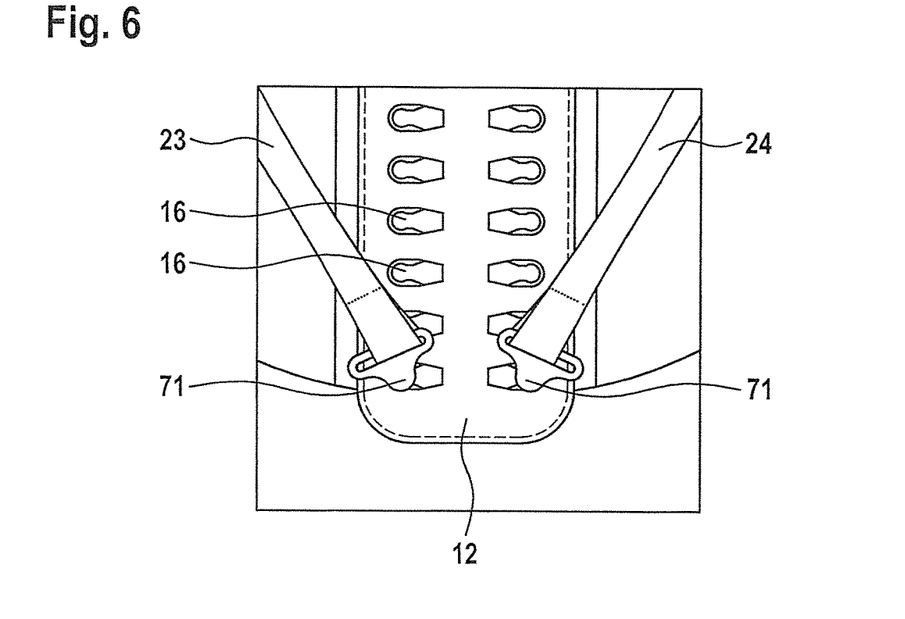
Figure 7:
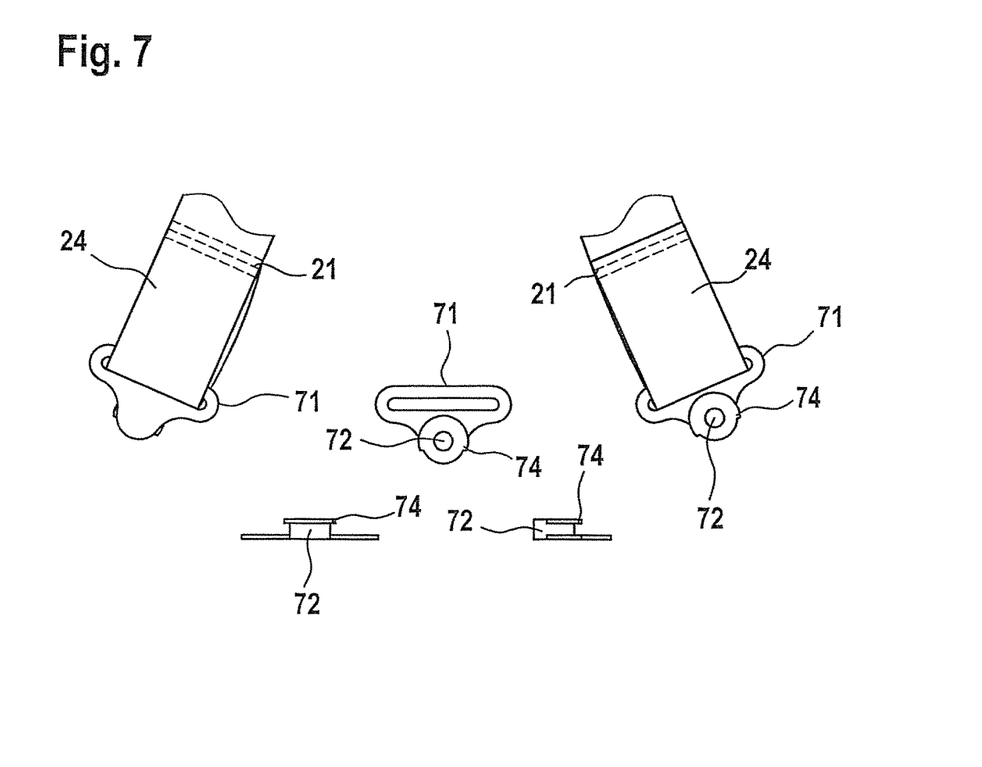

FIG. 6 shows a detailed view of the anchoring of straps 24 or 23 at caudal section 12 of the reclinator splint by means of anchor grommets 71, in which straps 24 or 23 are guided and fixated, respectively. Whereby anchor grommets 71 are affixable in a variable manner in anchoring points 16 that are formed at the reclinator splint. To this end, FIG. 7 shows detailed views of anchor grommets 71 in plan views and in sectional views. In this embodiment, the anchor grommets possess snap-in-nose 72 including an indentation and shoulder 74, which are specifically to snap in appropriately formed fixation points 16 of reclinator splint 10, and be protected from dropping out after turning the appropriate work angle because of shoulder 74. They are pivotable around snap-in-nose 72, however. In the depicted embodiment, after they had been guided through anchor grommets 71, the strap ends are firmly sewn onto connection areas 21, or they are attached to themselves with hooks and loops, or buttons, or hooks there.

Figure 8:
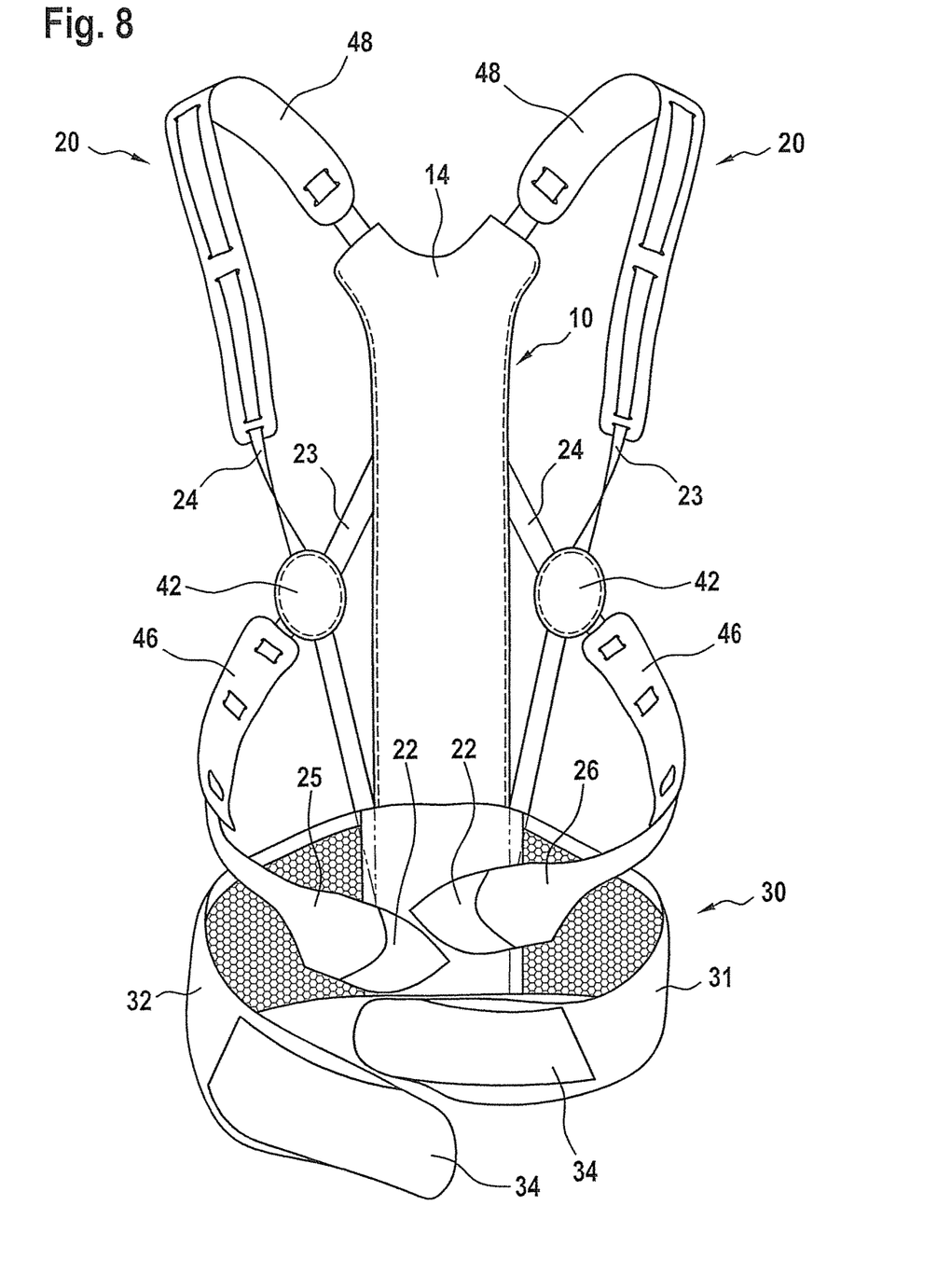

Finally, FIG. 8 depicts a comprehensive view of the reclination orthosis in accordance with the invention according to above FIGS. 1 through 7. The strap ends 25, 26 are preferably additionally provided with grab bags 22, which enable the patient to better grab strap ends 25, 26 for tensioning purposes. Fleece zones 34 of both bandage ends 31 and 32 are discernible, which are provided for their mutual hook-and-loop fastening on the one hand, and to accommodate strap ends 25, 26, which are provided with hook and loop fastener elements.

The invention claimed is:

1. A reclination orthosis configured to be worn by a person,
the reclination orthosis comprising:
a pelvic strap;
a rigid reclinator splint including:
a caudal section configured to be positioned in proximity to the dorsal section of the person, and
a cranial section configured to be positioned in proximity to the cranial and shoulder interface of the person; and
two individual tensile shoulder straps,
the shoulder straps forming an ipsilateral shoulder strap section, respectively, running upward from the caudal section of the reclinator splint, the caudal section of the reclinator splint defining a starting point of the shoulder straps,
the shoulder straps extending through guide grommets to the cranial section of the reclinator splint,
the shoulder straps crossing each other in a dorsal central cross point and contralaterally extending downwardly from the cranial section of the reclinator splint to cross in two lateral thoracic cross points with the respective upward running ipsilateral strap section and further extending towards a ventral section of the reclinator splint in proximity to a ventral section of the person with the respectively upward running ipsilateral shoulder strap section, and then ending in ventral strap ends,
the ventral strap ends being affixable at a ventral section of the pelvic strap, which is tensed,
the ventral strap ends being affixable at the reclinator splint in proximity to the ileosacral joint providing a reclination effect for the reclination orthosis.

2. The reclination orthosis according to claim 1, whereby the shoulder straps that extend ipsilaterally upward and further extend contralaterally downward cross at the two lateral thoracic cross points at roughly a right angle, respectively.

3. The reclination orthosis according to claim 1, whereby both shoulder straps run freely at the two lateral thoracic cross points, the dorsal central cross point and in the guide grommets and are exclusively fixated at the caudal section of the reclinator splint, and are affixable at the ventral strap ends of the shoulder straps at the ventral section of the pelvic strap.

4. The reclination orthosis according to claim 3, whereby the shoulder straps in both lateral thoracic cross points are guided in a free running manner in cross guides.

5. The reclination orthosis according to claim 4, whereby the reclination orthosis is configured wherein a supporting force to support the thoracic and lumbar spine of the person after applying the pelvic strap on the pelvis and iliac crest of the person can be fully generated by pulling both strap ends of both individually free running shoulder straps and affixing both individually free running shoulder straps under tension at the ventral section of the pelvic strap.

6. The reclination orthosis according to claim 3, whereby the shoulder straps in both lateral thoracic cross points are guided in cross guides.

7. The reclination orthosis according to claim 3, whereby the caudal section of the reclinator splint can be positioned at the level of the ileosacral joint of the person, and the cranial section of the reclinator splint can be positioned at the upper vertebra of the chest or vertebra of the neck of the person.

8. The reclination orthosis according to claim 3, whereby the shoulder straps are guided at the starting points of the shoulder straps at the caudal section of the reclinator splint, respectively, through anchor grommets where the shoulder straps are fixated, and whereby the anchor grommets are fixated in anchoring points formed at the reclinator splint.

9. The reclination orthosis according to claim 8, whereby the reclination splint exhibits several fixation points at least in the caudal section of the reclination splint, wherein the shoulder straps are affixable, respectively, by means of the anchor grommets, the position of the anchor grommets being variable to adapt to the reclination effect of the reclination splint, the reclination effect of the reclinator splint at least contributing to, or entirely providing, the reclination effect of the reclination orthosis.

10. The reclination orthosis according to claim 3, whereby the pelvic strap can be positioned on the pelvis and iliac crest below the abdomen of the person where the pelvic strap can be affixed under tension.

11. The reclination orthosis according to claim 1, whereby the shoulder straps in both lateral thoracic cross points are guided in a free running manner in cross guides.

12. The reclination orthosis according to claim 11, whereby the reclination orthosis is configured wherein a supporting force to support the thoracic and lumbar spine of the person after applying the pelvic strap on the pelvis and iliac crest of the person can be fully generated by pulling both strap ends of both individually free running shoulder straps and affixing both individually free running shoulder straps under tension at the ventral section of the pelvic strap.

13. The reclination orthosis according to claim 11, whereby the caudal section of the reclinator splint can be positioned at the level of the ileosacral joint of the person, and cranial section of the reclinator splint can be positioned at the upper vertebra of the chest section or vertebra of the neck portion of the person.

14. The reclination orthosis according to claim 11, whereby the shoulder straps are guided at the starting points of the shoulder straps at the caudal section of the reclinator splint, respectively, through anchor grommets where the shoulder straps are fixated, and whereby the anchor grommets are fixated in anchoring points formed at the reclinator splint.

15. The reclination orthosis according to claim 14, whereby the reclinator splint exhibits several fixation points at least in the caudal section wherein the shoulder straps are affixable, respectively, by means of the anchor grommets, the position of the anchor grommets being variable to adapt to the reclination effect of the reclinator splint, the reclination effect of the reclinator splint at least contributing to, or entirely providing, the reclination effect of the reclination orthosis.

16. The reclination orthosis according to claim 1, whereby the shoulder straps in both lateral thoracic cross points are guided in cross guides.

17. The reclination orthosis according to claim 1, whereby the caudal section of the reclinator splint can be positioned at the level of the ileosacral joint of the person, and the cranial section of the reclinator splint can be positioned at the upper vertebra of the chest section or vertebra of the neck of the person.

18. The reclination orthosis according to claim 1, whereby the shoulder straps are guided at the starting points of the shoulder straps at the caudal section of the reclinator splint, respectively, through anchor grommets where the shoulder straps are fixated, and whereby the anchor grommets are fixated in anchoring points formed at the reclinator splint.

19. The reclination orthosis according to claim 18, whereby the reclinator splint exhibits several fixation points at least in the caudal section wherein the shoulder straps are affixable, respectively, by means of the anchor grommets, the position of the anchor grommets being variable to adapt to the reclination effect of the reclinator splint, the reclination effect of the reclinator splint at least contributing to, or entirely providing, the reclination effect of the reclination orthosis.

20. The reclination orthosis according to claim 1, whereby the pelvic strap can be positioned on the pelvis and iliac crest below the abdomen of the person where the pelvic strap can be affixed under tension.

* * * * *